United States Patent [19]

James et al.

[11] Patent Number: 5,393,750
[45] Date of Patent: Feb. 28, 1995

[54] COMPOSITION, PROCESS AND USE

[75] Inventors: Mark R. James, Rossendale; Gordon A. Thomson, Ladybridge, both of Great Britain

[73] Assignee: Zeneca, Limited, London, England

[21] Appl. No.: 846,298

[22] Filed: Feb. 24, 1992

Related U.S. Application Data

[62] Division of Ser. No. 555,118, Jul. 19, 1990, Pat. No. 5,120,856.

Foreign Application Priority Data

Jul. 19, 1989 [GB] United Kingdom ............... 8916447

[51] Int. Cl.$^6$ ............... C07D 207/12; C07D 209/44; A01N 37/28; A01N 43/38; A01N 59/16
[52] U.S. Cl. ............... 514/184; 514/186; 548/403; 548/472; 548/542; 548/470; 548/542
[58] Field of Search ............... 548/403, 472, 542; 514/185, 184, 425, 416

[56] References Cited

U.S. PATENT DOCUMENTS 3,163,603 12/1964 LeSuer ............... 548/404
3,223,711 12/1965 Shibe ............... 548/404

*Primary Examiner*—David B. Springer
*Attorney, Agent, or Firm*—Cushman Darby & Cushman

[57] ABSTRACT

A compound of the general formula

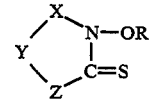

or a salt or complex thereof, in which X, Y and Z are all optionally substituted carbon atoms and R is hydrogen, optionally substituted hydrocarbyl or acyl or —COOR$^7$ and R$^7$ is hydrocarbyl has anti-microbial properties. Particular examples are compounds in which X is —CH$_2$— or —C(CH$_3$)$_2$— and Y and Z are both —CH$_2$— or X is is —CH$_2$— and Y and Z are carbon atoms of a benzene ring. The zinc complexes have useful properties.

14 Claims, No Drawings

COMPOSITION, PROCESS AND USE

This is a divisional application Ser. No. 07/555,118, filed on Jul. 19, 1990, U.S. Pat. No. 5,120,856.

The present invention relates to a class of compound, a process for the preparation of such compounds and the use of such compounds as industrial biocides.

Industrial biocides are useful to prevent industrial spoilage, in particular that caused by bacteria, fungi and algae. Materials which can be used as industrial biocides have antimicrobial properties, for example antifungal, antibacterial or antialgal properties and may even possess a combination of properties such as both useful antifungal and antibacterial properties. Such materials are useful in the preservation of products which are susceptible to attack by micro-organisms such as bacteria, fungi and algae. A wide range of products are susceptible to attack by micro-organisms and these products include paints, latices, adhesives, personal care products, leather, wood, plastics materials and additives to plastics materials, metal working fluids, cooling water and aqueous slurries.

In our European Patent Application Publication No 249328 we disclose a biocide composition which contains at least one compound of the formula

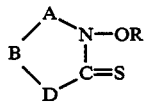

or a metal complex or salt thereof, the groups A, B and D being defined. Many compounds of this type are disclosed. The specific compounds disclosed are of the type thiazol-thione, imidazolidine-thione or imidazoline-thione. We have now found that compounds of the type pyrrolidine thione derivatives and pyrroline thione derivatives have useful anti-microbial properties.

According to the present invention there is provided a biocide composition which contains at least one compound of the formula I:

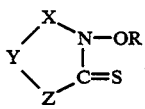

or a salt or complex thereof,
wherein
  X is a group —$CR^1R^2$— or a group —$CR^1$ =;
  Y is a group —$CR^3R^4$— or a group —$CR^3$ =;
  Z is a group —$CR^5R^6$— or a group —$CR^5$ =;
  R is hydrogen, a hydrocarbyl group, a substituted hydrocarbyl group, an acyl group, a substituted acyl group or a group —$COOR^7$;
  $R^1$ to $R^6$ are each, independently, a hydrogen atom, a hydrocarbyl group or a substituted hydrocarbyl group, or
  $R^1$ and $R^2$, together with the carbon atom to which they are attached, form a ring, and/or $R^3$ and $R^4$, together with the carbon atom to which they are attached, form a ring, and/or $R^5$ and $R^6$, together with the carbon atom to which they are attached, form a ring; or
  $R^1$ and $R^3$, together with the carbon atoms to which they are attached, form a ring or $R^3$ and $R^5$, together with the carbon atoms to which they are attached, form a ring; and
  $R^7$ is a hydrocarbyl group.

The groups X, Y and Z can form part of a further ring system but generally not more than two of the groups X, Y and Z form part of a further ring system. The further ring system is typically a ring system containing five or six atoms and may be a heterocyclic ring system but is preferably a hydrocarbon ring system, for example a cyclopentene, cyclohexane, cyclohexene, cyclohexadiene or benzene ring. The further ring system, if present, typically contains one or two carbon atoms from the groups X, Y, and Z. If only one group forms part of a ring system, this may be a cyclohexane ring of the type

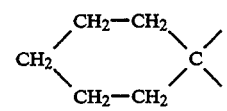

where the carbon atom of the group X, Y or Z is the carbon atom with the two free valencies, which are linked to the other groups in the pyrrolidine or pyrroline ring. If two of the groups X, Y and Z form part of a ring system, the further ring is then fused to the pyrrolidine or pyrroline ring system; for example when Y and Z both form part of a ring system such as a benzene ring as in 2-hydroxy-2,3-dihydro-1H-isoindol-1-thione.

Particularly useful biocide compositions in accordance with the present invention are those in which the group X is a group —$CR^1R^2$—, and especially is a group —$CH_2$— or —$C(CH_3)_2$—. The groups Y and Z my be groups —$CR^3R^4$— or —$CR^3$= and —$CR^5R^6$— or —$CR^5$= respectively. We have obtained useful biocide compositions using a compound in which the groups Y and Z are both —$CH_2$— groups. Useful results have also been obtained when the compound is one in which X is —$CH_2$— and Y and Z together form a benzene ring.

If any of the groups $R^1$ to $R^6$ are substituted groups, the substituents are typically selected from hydrocarbonoxy groups, acyl groups, ester (that is acyloxy) groups, a halogen atom or a group containing more than one halogen atom, for example a trifluoromethyl group, or a nitrile group.

The group R may be an acyl group, for example an acetyl group ($CH_3CO$). However, it is generally preferred that the biocide composition contains a salt or complex of the compound of general formula I. The salt or complex may be with an amine (including an alkanolamine) but more typically is with a metal, which may be any metal. Typically the metal present in the salt or complex is a transition metal, for example a metal of group VIII, IB or IIB of the Periodic Table. Such metals include iron, copper and zinc, particularly such metals in their maximum possible valency state.

All references herein to the Periodic Table are to the Periodic Table according to Mendeleeff, as set out on the inside rear cover of "General and Inorganic Chemistry" by J R Partington, Second Edition (1954) published by MacMillan and Co Limited, London.

For convenience hereafter, the compounds of the general formula I, and the salts and complexes thereof will be referred to simply as "compound I".

A wide range of compounds I can be used in the biocide compositions of the present invention. The compounds I have anti-microbial activity against a wide range of micro-organisms including bacteria, fungi and algae, and have useful anti-bacterial activity. Preferred compounds I have a useful combination of anti-bacterial, anti-fungal and anti-algal activity.

Compounds I which can be used in the compositions of the present invention include:
1-acetoxy-2-pyrrolidinthione;
1-acetoxy-5,5-dimethyl-2-pyrrolidinthione; and
2-hydroxy-2,3-dihydro-1H-isoindol-1-thione.
and the metal complexes and salts thereof. The metal salts and complexes thereof include ferric, cupric and zinc complexes and salts. Compositions of the present invention which contain metal salts or complexes are preferred, for example compositions which contain one of the following complexes:
2:1 complex of 2-hydroxy-2,3-dihydro-1H-isoindol-1-thione and zinc;
2:1 complex of 1-hydroxy-2-pyrrolidinthione and zinc; and
2:1 complex of 5,5-dimethyl-1-hydroxy-2-pyrrolidinthione and zinc.

The biocide composition of the present invention includes a carrier in addition to compound I. The carrier is typically a material which shows little, if any, antimicrobial activity and may be, or may include, a material which is susceptible to the growth of micro-organisms.

It is generally preferred that the carrier is a liquid medium and the biocide composition may be a solution, suspension or emulsion of compound I in a liquid carrier. The carrier may be water, in which a number of compounds of formula I, or the salts or complexes thereof, are essentially insoluble. Alternatively, the carrier may be a liquid such as acetic acid, N,N-dimethylformamide, propylene glycol, dimethyl sulphoxide or N-methyl-2-pyrrolidone in which many compounds of formula I, or the salts or complexes thereof, are soluble. Alternatively, a mixture of liquids may be used, one being a solvent for compound I and the other being a non-solvent, and using such a mixture the composition typically comprises an emulsion or droplets of a solution of compound I in the solvent therefore dispersed in the non-solvent. If a suspension or emulsion is used, this conveniently contains a surface active agent which is effective to maintain the non-continuous phase as a suspension or emulsion. Any surface active agent known for use in biocide compositions may be used in such a system, for example alkylene oxide adducts of fatty alcohols, alkyl phenols and amines such as ethylene diamine.

The carrier may be alternatively be a solid when the biocide composition is very conveniently a solid, particulate material. The solid carrier may be a water-insoluble carrier such as silica or alumina. However, for ease of dispersion into a medium to be treated, it is preferred that the carrier is a water-soluble material since many of the media to be treated are aqueous systems. Any water soluble material may be used as a carrier provided it does not react with, and adversely affect, the antimicrobial properties of compound I. One class of carrier which may be used in the water-soluble inorganic salts, particularly salt of monovalent metals especially the alkali metals. Compound I may be deposited onto the carrier using any known technique for depositing a material from solution onto a solid.

The amount of compound I which is present in the biocide composition may be just sufficient to have an antimicrobial effect or compound I may be present in a substantially greater proportion. It will be appreciated that the biocide composition may be provided as a concentrated solution which is subsequently diluted for use as an anti-microbial material. Thus, the amount of the compound I which is present in the biocide composition is typically in the range from 0.0001% up to 50% by weight of the biocide composition.

Some of the compounds used in the biocide composition of the present invention are new.

Thus, as a further aspect of the present invention there is provided a compound of the formula

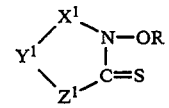

wherein:
$X^1$ is a group —$CR^1R^2$— or a group —$CR^1$=;
$Y^1$ is a group —$CR^3R^4$— or a group —$CR^3$=;
$Z^1$ is a group —$CR^5R^6$— or a group —$CR^5$=, and R and $R^1$ to $R^6$ are all as herein before defined, with the exceptions that
when $X^1$ is —$C(CH_3)_2$—, R is —H or —$CH_3$ and $Y^1$ is —$CH_2$—, $Z^1$ is neither —$CH_2$— nor —$C(CH_3)_2$—; and
when $X^1$ is —$C(CH_3)_2$—, R is —H or —$CH_3$ and $Z^1$ is —$CH_2$—, $Y^1$ is neither —$CH(CH_3)$— nor —$CH(C_6H_5)$—.

Preferred compounds in accordance with this further aspect of the present invention are those in which the group $X^1$ is a group —$CR^1R^2$— and especially is a group —$CH_2$—, subject to the exceptions as herein before defined.

As a yet further aspect of the present invention there is provided a salt or complex of a compound of the formula

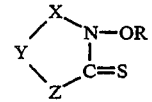

where R, X, Y and Z are all as hereinbefore defined.

In the compounds according to the yet further aspect of the present invention, it is preferred that the group X is a group —$CR^1R^3$ and especially is a group —$CH_2$— or a group —$C(CH_3)_2$—.

The salt or complex is especially one with a metal and materials having useful properties have been obtained in which the metal is zinc. Thus, particular materials in accordance with this aspect of the present invention are the salt or complex of 2-hydroxy-2,3-dihydro-1H-isoindol-1-thione and zinc; the salt or complex of 1-hydroxy-2-pyrrolidinthione and zinc and the salt or complex of 5,5-dimethyl-1-hydroxy-2-pyrrolidinthione and zinc.

Compounds of formula I may be prepared in a multistage procedure starting from 1,2 dialdehydes, and the product thus obtained may be further reacted to obtain a salt or complex if desired. More specifically, a dialdehyde is reacted with hydroxylamine to obtain a N-hydroxypyrrolidone or pyrrolinone derivative as an intermediate product. The intermediate product is treated with an acid halide such as acetyl chloride to esterify the N-hydroxy group, the esterified product is treated with Lawesson's reagent to obtain the acetyl thione. This acetyl derivative, which is a compound of formula I, is preferably hydrolysed to obtain a hydroxythione compound of formula I. A salt or complex is then obtained, if desired, by reaction with a metal salt, for example zinc acetate.

We have found that some hydroxythione compounds of formula I, that is compounds in which R is hydrogen, are somewhat unstable and may be difficult to isolate in a satisfactory yield. We have found that the desired salt or complex may be obtained directly from the acyl derivative by reaction with a trialkylsilanolate of the desired metal.

Thus, as a further feature of the present invention there is provided a process for preparing a metal salt or metal complex of a compound of formula I, wherein a trialkylsilanolate of the metal is reacted with a compound of formula I in which the group R is an acyl group.

The trialkylsilanolate is conveniently a trimethylsilanolate. The metal is conveniently zinc. The reaction is conveniently effected in the presence of a liquid medium which is a solvent for one or both of the reactants but which is preferably a non-solvent, or a poor solvent, for the desired metal salt or metal complex. A suitable liquid medium is tetrahydrofuran but other liquids such as diethyl ether, 1,4-dioxane, toluene, benzene or other aprotic liquids may be used as the liquid medium. The reaction is conveniently effected at ambient temperature or below, for example at 0° C. The reaction is preferably carried out in the essential absence of moisture for example using dry air or in an inert gaseous atmosphere such as nitrogen or argon.

The reaction product is conveniently insoluble in the reaction medium and forms a precipitate which can be isolated by any suitable means, for example by filtration. The process requires only a single stage and generally gives a higher yield of the metal salt or metal complex than is obtained by hydrolysis to form the hydroxy derivative followed by reaction to obtain the metal salt or metal complex.

As an alternative to using butanedial, a 1,2-dialdehyde, as a starting material to obtain 1-hydroxy-2-pyrrolidinone, we have prepared this compound from cyclobutanone. More specifically, cyclobutanone is reacted with N-hydroxybenzenesulphonamide in the presence of a base in a suitable liquid medium. The mixture is acidified to recover the desired hydroxy compound. The reaction is conveniently effected at ambient temperature or below, for example at an initial temperature of −10° C. and allowing to warm up to ambient temperature. Any suitable liquid medium may be used and we have obtained satisfactory results using aqueous ethanol as the liquid medium.

A convenient process for the preparation of a metal salt or metal complex of a compound of formula I comprises the steps of 1) reacting a 1-hydroxy-2-pyrrolidinone or 1-hydroxy-2-pyrrolinone derivative with an acid halide; and
2) reacting the product of step 1 with Lawesson's reagent.

The product of step 2 in the foregoing process is a 1-acyloxy-2-pyrrolidinthione compound of formula I. This may be the desired product but generally it is preferred that the final product is a salt or complex of a compound of formula I. Such a product may be obtained by hydrolysis of the acyloxy compound to obtain the corresponding hydroxy compound and reacting this hydroxy compound with a salt, particularly a metal salt, to obtain the desired salt or complex. However, as noted previously herein, a salt or complex can be obtained by reacting the acyloxy compound with a metal trialkylsilanolate and we generally prefer to prepare a metal salt or metal complex of the compound of formula I by reaction of the acyloxy compound with a metal trialkylsilanolate.

Compound I, typically has anti-bacterial, anti-fungal and anti-algal activity and preferred Compounds I have useful anti-bacterial, anti-fungal and anti-algal activity. Hence, compound I, or biocide compositions containing compound I, can be used for the treatment of various media to inhibit the growth of micro-organisms.

As a further aspect of the present invention there is provided a method for inhibiting the growth of micro-organisms on, or in, a medium which comprises treating the medium with compound I or a biocide composition containing compound I.

Compound I or the biocide composition can be used in conditions in which micro-organisms, especially fungi, bacteria and/or algae, grow and cause problems. Systems in which micro-organisms cause problems include liquid, particularly aqueous, systems such as cooling water liquors, metal working fluids, geological drilling lubricants, polymer emulsions and surface coating compositions such as paints, varnishes and lacquers and also solid materials such as wood and leather. Compound I or the biocide composition can be included in such materials and is particularly useful when incorporated into a paint, varnish or lacquer to which they provide anti-microbial characteristics.

As a particular aspect of the present invention there is provided a surface coating composition which contains an effective amount of compound I The surface coating composition may be a paint, varnish or lacquer and is especially a paint, for example an emulsion paint. The amount of compound I which is present in the surface coating composition is typically in the range from 0.001 up to 2% by weight and especially 0.1 up to 1% by weight relative to the total weight of the surface coating composition. Compound I can provide a range of anti-microbial characteristics, for example anti-fungal properties, and also anti-algal properties, to the surface coating composition when applied to a surface and can also provide anti-bacterial properties which are useful for in-can preservation of the surface coating composition.

Compound I may be the only antimicrobial compound or may be used in a biocide composition which includes other compounds having antimicrobial characteristics. Thus, a mixture of different compounds of formula I, or salts or complexes thereof, may be used. Alternatively, at least one compound of the formula I, or a salt or complex thereof, may be used together with one or more known antimicrobial compounds. The use of a mixture of anti-microbial compounds can provide a composition having a broader anti-microbial spectrum and hence one which is more generally effective than the components thereof. The known anti-microbial may be one possessing anti-bacterial, anti-fungal, anti-algal or other anti-microbial characteristics. The mixture of compound I with other anti-microbial compounds typically contains from 1 to 99% by weight, relative to the weight of total antimicrobially active compounds, of Compound I particularly from 40 to 60% by weight of Compound I.

As examples of known antimicrobial compounds which may be used, together with Compound I, there may be mentioned quarternary ammonium compounds such as diethyldodecylbenzyl ammonium chloride; dimethyloctadecyl-(dimethylbenzyl)ammonium chloride; dimethyldidecylammonium chloride; dimethyldidodecylammonium chloride; trimethyl-tetradecylammonium chloride; benzyldimethyl($C_{12}$-$C_{18}$ alkyl)ammonium chloride; dichchlorobenzyldimethyldodecylammonium chloride; hexadecylpyridinium chloride; hexadecylpyridinium bromide; hexadecyltrimethylammonium bromide; dodecylpyridinium chloride; dodecylpyridinium bisulphate; benzyldodecylbis(beta-hydroxyethyl)-ammonium chloride; dodecylbenzyltrimethylammonium chloride; benzyldimethyl($C_{12}$-$C_{18}$ alkyl)ammonium chloride; dodecyldimethylethyl ammonium ethylsulphate; dodecyldimethyl-(1-naphthylmethyl)ammonium chloride; hexadecyldimethylbenzyl ammonium chloride; dodecyldimethylbenzyl ammonium chloride and 1-(3-chloroallyl)-3,5,7-triaza-1-azonia-adamatane chloride; urea derivatives such as 1,2-bis(hydroxymethyl)-5,5-dimethylhydantoin; bis(hydroxymethyl)urea; tetrakis(hydroxymethyl)acetylene diurea; 1-(hydroxymethyl)-5,5-dimethylhydantoin and imidazolidinyl urea; amino compounds such as 1,3-bis(2-ethyl-hexyl)-5-methyl-5-aminohexahydropyrimidine; hexamethylene tetra amine; 1,3-bis(4-aminophenoxy)propane; and 2-[(hydroxymethyl)amino]ethanol; imidazole derivatives such as 1[2-(2,4-dichlorophenyl)-2-(2-propenyloxy)ethyl]-1H-imidazole; 2-(methoxycarbonyl-amino)-benzimidazole; nitrile compounds such as 2,4,5,6-tetra-chloroisophthalodinitrile and 1,2-dibromo-2,4-dicyanobutane; thiocyanate derivatives such as methylene bis thiocyanate; zinc compounds or complexes such as zinc-2-pyridine-thiol-N-oxide; tin compounds or complexes such as tributyltin-oxide, chloride, naphthoate, benzoate or 2-hydroxybenzoate; thiazole derivatives such as 2-(thiocyanomethylthio)-benzthiazole; and mercaptobenzthtazole; isothiazole derivatives such as 5-chloro-2-methyl-4-isothiazolin-3-one and magnesium salts thereof; 2-methyl-4-isothiazolin-3-one; 1,2-benzisothiazolin-3-one and the alkali metal, ammonium and amine salts thereof; and 2-n-octyl-4-isothiazolin-3-one; nitro compounds such as tris(hydroxymethyl)nitromethane, 5-bromo-5-nitro-1,3-dioxane and 2-bromo-2-nitropropane-1,3-diol; aldehydes and derivatives such as gluteraldehyde (pentanedial) p-chlorophenyl-3-iodopropargyl formaldehyde and glyoxal; amides such as chloracetamide, N,N-bis(hydroxymethyl)chloracetamide, N-hydroxymethyl-chloracetamide and dithio-2,2-bis(benzmethyl amide); guanidine derivatives such as poly hexamethylene biguanide and 1,6-hexamethylene-bis[5-(4-chlorophenyl)biguanide]; thiones such as 3,5-dimethyltetrahydro-1,3,5-2H-thiodiazine-2-thione; triazine derivatives such as hexahydrotriazine and 1,3,5-tri-(hydroxyethyl)-1,3,5-hexahydrotriazine; oxazolidine and derivatives thereof such as bis-oxazolidine; furan and derivatives thereof such as 2,5-dihydro-2,5-dialkoxy-2,5-dialkylfuran; carboxylic acids and the salts and esters thereof such as sorbic acid and the salts thereof and 4-hydroxybenzoic acid and the salts and esters thereof; phenol and derivatives thereof such as 5-chloro-2-(2,4-dichlorophenoxy) phenol, thio-bis(4-chlorophenol) and 2-phenylphenol; sulphone derivatives such as diiodomethyl-paratolyl sulphone, 2,3,5 6-tetrachloro-4 (methylsulphonyl) pyridine and hexachlorodimethyl sulphone.

Compound I is particularly useful when incorporated into a surface coating composition and hence, if used with other compounds having antimicrobial characteristics, these other compounds are advantageously compounds of the type used in surface coating compositions. Compounds which may be used in surface coating compositions include, inter-alia, anti-bacterial agents such as imidazolidinyl urea: 1, 2-dibromo-2,4-dicyanobutane; 5-chloro-2-methyl-4-isothiazolin-3-one and the magensium salts thereof; 2-methyl-4-isothiazolin-3-one; 1,2-benzisothiazolin-3-one and the salts thereof; 2-bromo-2-nitropropane-1, 3-diol; gluteraldehyde; poly hexamethylene biguanide; triazine derivatives and oxazolidine and derivatives thereof. Surface coating compositions may also include anti-fungal agents such as 1[2-(2, 4-dichlorophenyl)-2-(2-propenyloxy) ethyl]-1H-imidazole; 2-(methoxycarbonylamino)-benzimidazole; 2,4,5,6-tetrachloroisophthalodinitrile; zinc-2-pyridinethiol-N-oxide; 2-(thiocyanomethylthio)-benzthiazole; 2-n-octyl-4-thiazolin-3-one; dithio-2, 2-his (benzmethyl amide); diiodomethyl-paratolysulphone and 2,3,5,6-tetrachloro-4 (methylsulphonyl) pyridine.

Further aspects of the present invention are described in the following illustrative examples. In the following tests and examples, all parts are by weight unless stated to the contrary.

In the following examples, the products obtained were subjected to microbiostatic evaluation. The microbiological testing was effected, under sterile conditions throughout, as follows:

In the microbiological testing, the products were tested for anti-microbial activity against bacteria and fungi. The bacteria used were one or more of *Escherichia coli, Pseudomonas aeruginosa, Staphylococcus aureus* and *Bacillus subtiles*. The fungi used were one or more of *Alternaria alternata, Aspergillus niger, Aureobasidum pullulans, Cladosporium sphaerospermum, Cladosporium herbarum, Penicillium pinophilum, Gliocladium roesum* and *Chaetomium globosum*. Testing against the yeast, candida albicans was also carried out in some cases. Anti-algal testing was also carried out as is described in more detail in Examples 13 to 16.

These test organisms will be referred to hereafter as EC, PA, SA, BS, AA, AN, AP, CS, CH, PP, GR, CG and CA respectively.

MICROBIOSTATIC EVALUATION

A) Agar test

The material to be tested was dissolved in a suitable solvent and the solution obtained diluted with a further quantity of the same solvent to give a desired product concentration.

To a suitable agar medium was added a quantity of the product solution to give a desired concentration of the product. The agar medium containing the product was poured into petri dish plates and allowed to set.

The test organisms were surface inoculated onto the test plates by means of a multi-point inoculator. Each test plate was inoculated with both bacteria and fungi. The plates were incubated for four days at 25° C.

At the end of the incubation period, the plates were assessed visually for growth of the micro-organisms. The concentration of the product which inhibited the growth of a particular micro-organism was recorded.

B) Microtitre Assay

A sample of the product to be tested was either dissolved in N,N-dimethylformamide to give a concentration of 5 g. dm$^{-3}$ or, with a product which is insoluble in N,N-dimethylformamide, the product is dispersed in water by milling in water for at least 72 hours to give a dispersion concentration of 5 g. dm$^{-3}$.

For testing against bacteria, 0.1 cm$^3$ of a fresh stationary phase culture of the bacterium (having at least 10$^8$ cells per cm$^3$) were added to 100 cm$^3$ of nutrient broth and mixed. 0.1 cm$^3$ aliquots of the mixture were dispensed into microtitre wells with the exception of the first row of the plate into which an 0.2 cm$^3$ aliquot was placed. 0.02 cm$^3$ of the solution or dispersion of the product to be tested was added to the first well (which contained an 0.2 cm$^3$ aliquot) and mixed. 0.1 cm$^3$ of this mixture was removed, transferred to the well in the adjacent row and mixed, this serial dilution procedure being effected across the plate until the last well when 0.1 cm$^3$ was discarded. Incubation was effected for 24 hours at 37° C.

For testing against fungi a similar procedure was used with the following modifications:

A fresh spore suspension of the fungus was made up in sterile saline (this contained 10$^9$ cells per cm$^3$) and was used instead of a stationary phase culture. Malt broth was substituted for nutrient broth. Incubation was effected for 72 hours at 25° C.

Any precipitation of the compound being tested was noted before incubation since precipitation could interfere with assessment of the results. At the end of the incubation period, the plates were assessed visually for inhibition of growth of the micro-organisms. The concentration of the product which inhibited the growth of a particular micro-organism was recorded.

EXAMPLE 1

A. Preparation of 2-hydroxy-2,3-dihydro-1H-isoindol-1-one

The procedure was in accordance with the method of O Neunhoeffer and G Gottshelch Ann. Chem 1970, (736) 100.

A solution of 13.4 g (0.1 mol) of phthalic dicarboxaldehyde in methanol (30 cm$^3$) was added to a solution of 6.9 g (0.1 mol) of hydroxylamine hydrochloride and 10 g (0.094 mol) of sodium carbonate in water (200 cm$^3$).

The mixture was stirred at ambient temperature until reaction was complete as determined by thin layer chromatography (tlc) (about 6 hours). The solution was washed with chloroform (10 cm$^3$), the pH was adjusted to seven by the addition of normal hydrochloric acid and the neutral solution was extracted with chloroform (4×40 cm$^3$). The combined chloroform extracts were chilled to 4° C. overnight to yield a grey solid which was crystallised from a 1:1 by volume mixture of chloroform and diethyl ether. 2-hydroxy-2,3-dihydro-1H-isoindol-1-one having a melting point of 191 - 2° C., was obtained in a yield of 2.38 g (16%). By analysis the product was found to contain C, 64.0% wt., H 4.7% wt. and N 9.3% wt. C$_8$H$_7$NO$_2$ requires C 64.4% wt., H 4.7% wt., H 4.7% wt. and N 9.4% wt. The mass spectral data is consistent with the product being 2-hydroxy-2,3-dihydro-1H-isoindol-1-one.

B. Preparation of 2-Acetoxy-2,3-dihydro-1H-isoindol-1-one 2.24 g (15.0 mmol) of 2-hydroxy-2,3-dihydro-1H-isoindol-1-one, obtained as described in Part A, 1.26 g (15.0 mmol) of sodium hydrogen carbonate and 2.0 g of a 4Å molecular sieve were added to dry dichloromethane (50 cm$^3$). The mixture was stirred, cooled on ice and a solution of 3.53 g (45.0 mmol) of acetyl chloride in dichloromethane (20 cm$^3$) was added over 10 minutes. The solution was allowed to warm to ambient temperature and, after two hours at ambient temperature, a further 3.53 g (45.0 mmol) of acetyl chloride, together with 2.07 g (15.0 mmol) of potassium carbonate were added. The resulting mixture was stirred overnight at room temperature, filtered and evaporated to a crude grey solid. 2-acetoxy-2,3-dihydro-1H-isoindol-1-one having a melting point of 69°–71° C. was obtained in a yield of 2.62 g (99%). The infra red absorption spectrum showed peaks at 1800, 1705, 1152, 1003 and 729 cm$^{-1}$. The mass spectral data is consistent with the product being 2-acetoxy-2,3-dihydro-1H-isoindol-1-one.

C. Preparation of 2-hydroxy-2,3-dihydro-1H-isoindol-1-thione 2.33 g (13.2 mmol) of crude 2-acetoxy-2,3-dihydro-1H-isoindol-1-one, prepared as described in Part B, were dissolved in dry dichloromethane (100 cm$^3$), 5.66 g (14.0 mmol) of Lawesson's reagent were added and the mixture refluxed for 48 hours, at which time tlc indicated reaction was complete. The organic mixture was evaporated to a dark green sludge which was dissolved in a mixture of tetrahydrofuran (14 cm$^3$) and water (10 cm$^3$). The mixture was stirred at 50° C. and an aqueous sodium hydroxide solution was added dropwise to maintain the pH at 8–9. Once the pH had stabilised, the aqueous mixture was stirred for a further hour before cooling to 0° C. and adding a further quantity of the aqueous sodium hydroxide solution to raise the pH to 10. The basic solution was washed with diethyl ether (4×50 cm$^3$), acidified with 6 M aqueous hydrochloric acid and extracted with diethyl ether (4×50 cm$^3$). The combined diethyl ether extracts were washed with water, dried over anhydrous magnesium sulphate and evaporated to an orange oil. This was flash chromatographed on silica with a petroleum ether (60–80) ethyl acetate mixture of varying composition as eluant. The ferric chloride positive fractions were combined and evaporated. The residue was purified by dissolving in toluene, adding charcoal, stirring the mixture, filtering to remove the charcoal and then crystallising. 2-hydroxy-2,3-dihydro-1H-isoindol-1-thione, having a melting point of 110-1° C. was obtained in a yield of 0.33 g (15%). By analysis the product was found to contain C 58.5% wt. and H 4.3% wt. C$_8$H$_7$NOS requires C 58.2% wt. and H 4.2% wt. The infra red absorption spectrum showed peaks at 1497, 1335, 1290 and 1203 cm$^{-1}$. The proton n.m.r. spectrum and mass spectral data are consistent with the product being 2-hydroxy-2,3-dihydro-1H-isoindol-1-thione.

D. Preparation of 2-hydroxy-2,3-dihydro-1H-isoindol-1-thione zinc complex (2:1)

200 mg (1.2 mmol) of 2-hydroxy-2,3-dihydro-1H-isoindol-1-thione, obtained as described in Part C, were dissolved in methanol (20 cm$^3$) and a solution of 140 mg (0.6 mmol) of zinc acetate in methanol (20 cm$^3$) was added. A grey precipitate appeared. Distilled water (40 cm$^3$) was added, the crude product was collected and then crystallised from chlorobenzene. 2-hydroxy-2,3-dihydro-1H-isoindol-1-thione zinc complex (2:1) having a melting point of 259° C. was obtained in a yield of 200 mg (84%). By analysis the product was found to contain C 48.0% wt., H 3.0% wt. and N 6.8% wt. $C_{16}H_{12}N_2O_2S_2$ Zn+1% $H_2O$ requires C 48.3% wt., H 3.15% wt. and N 7.0% wt. The infra red absorption spectrum showed peaks at 1501, 1297, 1212, 762 and 689 $cm^{-1}$. The proton n.m.r. spectrum and mass spectral data are consistent with the product being a 2:1 complex.

This material will be referred to as "Compound 1".

EXAMPLE 2

A. Preparation of 1-Hydroxy-2-pyrrolidinone

To a solution of 5.19 g (30 mmol) of N-hydroxybenzenesulphonamide in ethanol (30 $cm^3$) at −10° C. (salt ice bath) were added 30 $cm^3$ of a 1 N aqueous solution of sodium hydroxide (30 mmol) with stirring. After 10 minutes, 2.1 g (30 mmol) of cyclobutanone were added and the mixture was stirred at −10° C. for a further one hour. The mixture was allowed to warm up to ambient temperature and left for two days. The mixture was acidified with 30 $cm^3$ of 1.1 N hydrochloric acid, evaporated and the residue purified by silica-gel chromatography using ethyl acetate as the initial eluant, progressively containing a higher proportion of methanol, up to 20% methanol by volume. 2.22 g (73% yield) of the product were obtained as a syrup. A small sample of this product was crystallised from toluene and was found to have a melting point of 62° C. By analysis the product was found to contain C 47.0% wt., H 7.8% wt. and N 13.7% wt. $C_4H_7NO_2$ requires C 47.5% wt., H 6.9% wt., and N 13.86% wt. Proton n.m r and $C^{13}$ n.m.r. spectra, and the mass spectral data, were consistent with the product being 1-hydroxy-2-pyrrolidinone.

B. Preparation of 1-Acetoxy-2-pyrrolidinone

To a stirred mixture of 2.0 g (19.8 mmol) of 1-hydroxy-2-pyrrolidinone, prepared as described in Part A, 4.0 g (47.5 mmol) of sodium hydrogen carbonate, 5 g of a 4A molecular sieve and 60 $cm^3$ dry dichloromethane at 0° C. were added 9.33 g (0.119 mol) of acetyl chloride. The mixture was allowed to warm up to ambient temperature and was stirred at ambient temperature for 24 hours. The mixture was filtered and the liltrate evaporated. The residue of the evaporation was purified by silica-gel chromatography using a 1:1 petroleum ether/ethyl acetate mixture as the initial eluant, progressively containing more ethyl acetate to 100% ethyl acetate. 2.77 g (982 yield) of the product were obtained as a syrup.

The infra red absorption spectrum showed peaks at 2924, 1797, 1714, 1460, 1393, 1359, 1269, 1178 and 1043 $cm^{-1}$. The proton n.m.r. spectrum was consistent with the product being 1-acetoxy-2-pyrrolidinone.

C. Preparation of 1-Acetoxy-2-pyrrolidinthione

A mixture of 2.64 g (18.46 mmol) of 1-acetoxy-2-pyrrolidinone, prepared as described in Part B, 7.47 g (18.46 mmol) of Lawesson's reagent and 70 $cm^3$ dry dichloromethane was heated under reflux with stirring for four hours. The mixture was cooled to ambient temperature, and filtered. The filtrate was evaporated to dryness and the residue purified twice by silica-gel chromatography using a mixture of hexane and ethyl acetate as eluant, initially a 2:1 volume mixture containing a progressively higher proportion of ethyl acetate to a 1:1 volume mixture. 2.8 g (95% yield) of the product were obtained as a syrup. The infra red absorption spectrum showed peaks at 2891, 1793, 1501, 1449, 1420, 1367, 1303, 1276 and 1156 $cm^{-1}$. Proton n.m.r. and $C^{13}$ n.m.r. spectra, and the mass spectral data, were consistent with the product being 1-acetoxy-2-pyrrolidinthione.

This material will be referred to as "Compound 2".

EXAMPLE 3

A. Preparation of Zinc trimethylsilanolate

100 $cm^3$ of a 0.5 M solution of zinc bromide in dry tetrahydrofuran were cooled to 0° C. and stirred under argon. To this solution were added, dropwise, 100 $cm^3$ of a 1 M solution of sodium trimethylsilanolate in dry tetrahydrofuran. The mixture was allowed to warmup to ambient temperature and was stirred overnight. The mixture was filtered. The filtrate was used as a 0.25 M solution of zinc trimethylsilanolate in tetrahydrofuran.

B. Preparation of 1-Hydroxy-2-pyrrolidinthione zinc complex (2:1)

To 0.267 g (1.68 mmol) of 1-acetoxy-2-pyrrolidinthione, prepared as described in Part C of Example 2, under argon at 0° C. were added, with stirring, 3.36 $cm^3$ of the solution of zinc trimethylsilanolate in tetrahydrofuran obtained in Part A. After 18 hours, a solid product (96 mg) was collected by filtration and washed with 5 $cm^3$ of tetrahydrofuran. A further crop of a solid product (50 mg) was obtained by partial evaporation of the filtrate. The combined solid product (0.146 g, 59% yield) had a melting point of 202° C. By analysis the product was found to contain:- C 32.1% wt.; H 4.1% wt. and N 9.2% wt. $C_8H_{12}N_2O_2S_2Zn$ requires C 32.27% wt., H 4.06% wt. and N 9.41% wt. The infrared spectrum showed peaks at 2948, 1558, 1312, 1151 and 1142 $cm^{-1}$. Proton n.m.r. and mass spectral data were consistent with the product being a 2:1 complex.

This material will be referred to as "Compound 3"

EXAMPLE 4

A. Preparation of 1-Acetoxy-5,5-dimethyl-2-pyrrolidinone

To a stirred mixture of 2.8 g (21.7 mmol) of 5,5-dimethyl -1-hydroxy-2-pyrrolidinone, prepared as described in J. Chem. Soc (1959) pages 2094–2102, 4.38 g (52.1 mmol) of sodium hydrogen carbonate, 7.0 g of 4A molecular sieve and 60 $cm^3$ dry dichloromethane, cooled to 0° C. were added 10.22 g (0.13 mol) of acetyl chloride.

The mixture was allowed to warmup to ambient temperature and stirred at ambient temperature for four hours. The mixture was filtered and the liltrate evaporated. The residue of the evaporation was purified by silica-gel chromatography using a 1:1 volume mixture of petroleum ether and ethyl acetate as the initial eluant, progressively containing more ethyl acetate to 100% ethyl acetate. 3.7 g (100% yield) of the product was obtained as a syrup. The infra red absorption spectrum showed peaks at 2969, 1794, 1718, 1396 and 1190 $cm^{-1}$. The proton n.m.r. spectrum was consistent with the product being 1-acetoxy-5,5-dimethyl-2-pyrrolidinone.

B. Preparation of 1-Acetoxy-5,5-dimethy-2-pyrrolidinthione

A mixture of 3.30 g (20.5 mmol) of 1-acetoxy-5,5-dimethyl-2-pyrrolidinone, prepared as described in Part A, 8.29 g (20.5 mmol) of Lawesson's reagent and 70 $cm^3$ of dry dichloromethane was heated under reflux with stirring for 3.75 hours. The mixture was cooled to ambient temperature and filtered. The filtrate was evaporated to dryness and the residue purified by silica-gel chromatography using a 4:1 volume mixture, changing progressively to a 2:1 volume mixture, of petroleum ether and ethyl acetate as eluant. The product was crystallised from a 1:1 petroleum ether/ethyl acetate mixture. 2.65 g (74% yield) of a solid having a melting point of 90°–91° C. were obtained. By analysis the solid product was found to contain C 51.5% wt.; H 7.4% wt.; N 7.2% wt. and S 16.9% wt. $C_8H_{13}NO_2S$ requires C 51.31% wt.; H 7.00% wt.; N 7.4% wt. and S 17.12% wt. The infra red absorption spectrum showed peaks at 2974; 1800; 1443; 1410; 1366; 1201; 1163 and 1078 cm$^{-1}$. Proton n.m.r. and mass spectral data were consistent with the product being 1-acetoxy-5,5-dimethyl-2-pyrrolidinthione.

This material will be referred to as "Compound 4".

EXAMPLE 5

A. Preparation of 5,5-Dimethyl-1-hydroxy-2-pyrrolidinthione zinc complex (2:1)

To 1.0 g (5.35 mmol) of 1-acetoxy-5,5-dimethyl-2-pyrrolidinthione, prepared as described in Part B of Example 4, under argon were added, with stirring, 32.1 cm$^3$ of the solution of zinc trimethylsilanolate in tetrahydrofuran obtained in Part A of Example 3. The solution of the zinc compound was added in three equal portions over two days (at 0,1 and 2 days). After a further day, 1 cm$^3$ of water was added, the mixture was evaporated and the residue purified by silica-gel chromatography using a 9:1 volume mixture, changing progressively to a 2:1 volume mixture, of petroleum ether and ethyl acetate as the eluant. The product was recrystallised from 1:1 volume hexane-ethyl acetate mixture. 0.55 g (58.5% yield) of a solid product having a melting point of 174°–176° C. was obtained. By analysis the solid product was found to contain C 41.2% wt.; H 6.0% wt.; N 7.3% wt. and S 17.0% wt. $C_{12}H_{20}O_2S_2N_2Zn$ requires C 40.74% wt.; H 5.7% wt.; N 7.9% wt. and S 18.12% wt. The infra red absorption spectrum showed peaks at 2972, 1546 and 1208 cm$^{-1}$.

The proton n.m.r. spectrum, and mass spectral data are consistent with the product being a 2:1 complex.

This material will be referred to as "Compound 5".

EXAMPLE 6 TO 9

The products of Examples 1,3,4 and 5 were evaluated against a range of micro-organisms using the procedure of the Microtitre Assay as herein before described. Control of the test organisms was obtained at the levels set out in the Table One.

TABLE ONE

| Test Organism (a) | COMPOUND (b) | | | | | |
|---|---|---|---|---|---|---|
| | 1 (ppm) | 3 (ppm) | 4 (ppm) | 5 (ppm) | A (ppm) | B (ppm) |
| EC | 2 | 4 | <4 | 1 | 4 | 8 |
| PA | 16 | 16 | 125 | 8 | 16 | 32 |
| BS | 1 | 1 | ND | <0.25 | 4 | 2 |
| AA | 2 | 4 | ND | 1 | 2 | 31 |
| AN | 2 | 16 | 31 | 8 | 2 | 8 |
| AP | 4 | 8 | ND | <0.25 | 1 | 2 |
| CH | 8 | 4 | ND | 8 | 1 | 4 |

TABLE ONE-continued

| Test Organism (a) | COMPOUND (b) | | | | | |
|---|---|---|---|---|---|---|
| | 1 (ppm) | 3 (ppm) | 4 (ppm) | 5 (ppm) | A (ppm) | B (ppm) |
| CG | 4 | 4 | ND | 8 | 1 | 4 |

Notes to Table One
(a) Organisms are as previously defined herein, the specific strains used being
EC NCIB 9132
PA NCIB 10421
BS NCIB 1650
AA PRA F54
AN CMI 17454
AP PRA F51
CH CMI 16203
CG PRA F55

(b) 1,3,4 and 5 are Compounds 1,3,4, and 5 as previously defined herein.
A is a complex as obtained in Example 2 of European Patent Application Publication No 249328.
B is a complex as obtained in Example 17 of European Patent Application Publication No 249328.
ND means "Not Determined", the product was not tested against this test organism.

The lowest level of product tested was 0.25 ppm with the exception of compound 4 which was tested to a lowest level of 4 ppm.

EXAMPLES 10 TO 12

The products of Examples 2,3 and 5 were evaluated against a range of micro-organisms using the procedure of the Agar test as hereinbefore described. Control of the test organisms was obtained at the levels set out in Table Two.

TABLE TWO

| Test Organism (a) (c) | COMPOUND (b) (d) | | |
|---|---|---|---|
| | 2 (ppm) | 3 (ppm) | 5 (ppm) |
| EC | ≦25 | ≦25 | ≦25 |
| PA | 500 | ≦25 | 100 |
| SA | ≦25 | ≦25 | ≦25 |
| BS | ND | ≦25 | ≦25 |
| AN | 500 | 100 | 100 |
| AP | ≦25 | ≦5 | ≦5 |
| CS | 500 | ND | ND |
| AA | ≦25 | ND | ND |
| CG | 500 | ND | ND |
| GR | ND | ≦5 | ≦5 |
| PP | ND | ≦5 | ≦5 |
| CA | ND | >100 | >100 |

Notes to Table Two
(a) and (b) are both as defined in Notes to Table One, with the exceptions noted in (c) in respect of the test organisms.
(d) ≦ indicates that the product provided control of the test organism at the lowest level of product tested.
> indicates that the product failed to control the test organism at the highest level of the product tested.

(c) Organisms are as previously defined herein and in Note (a) to Table One, the strains being:

| EC | NCTC | 5934 |
| SA | NCIB | 9518 |
| AP | CMI | 145194 |
| GR | CMI | 260419 |
| PP | CMI | 114933 |
| CA | NCYC | 597 |

EXAMPLES 13 TO 16

The products of Examples 1, 3, 4 and 5 were evaluated against an algal medium using the following procedure:

10 cm³ aliquots of an algal broth medium were placed in test tubes which were then capped. A chemical under test was added to the medium to give concentrations of from 0.16 ppm to 10 ppm of the chemical.

Each test tube was inoculated with 0.1 cm³ of a mixed algal suspension which was a 7 day culture of a mixture of the following algae:

*Stichococcus bacillaris*
*Gloecapsa alpicola*
*Nostoc commune*
*Trentepohlia aurea*

The test tubes were incubated at ambient temperature (15°-20° C.) with artificial illumination of between 700 and 1200 LUX provided to give 16 hours of illumination and 8 hours of darkness in every 24 hour period. After two weeks, the contents of the test tube were re-inoculated with 0.1 cm³ of the mixed algal suspension as described previously.

The incubation with alternate periods of light and dark was continued for a period of a further four weeks. The contents of the test tubes were then assessed visually for algal growth. The concentration of each chemical which completely inhibited algal growth was noted and the results are set out in Table Three.

TABLE THREE

| Ex or Comp Ex (e) | Compound Type (b) | ppm |
|---|---|---|
| 13 | 1 | 2.5 |
| 14 | 3 | 2.5 |
| 15 | 4 | 10 |
| 16 | 5 | 0.64 |
| C* | NIL | NIL |

Notes to Table Three
(b) is as defined in Notes to Table One
(e)* Extensive growth of algae was observed with a pronounced green colouration after seven days.

We claim:

1. A biocide composition which contains an effective amount of at least one compound of the formula I:

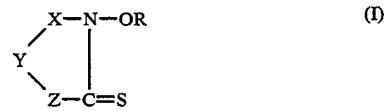

or a salt or complex thereof with a metal of group VIII, IB or IIB of the Periodic Table, together with a carrier material, wherein X is a group $-CR^1R^2-$ or a group $-CR^1=$;
Y is a group $-CR^3R^4-$ or a group $-CR^3=$;
Z is a group $-CR^5R^6-$ or a group $-CR^5=$;
R is a hydrogen or an acyl group; and
$R^1$ to $R^6$ are each, independently, a hydrogen atom or a $C_{1-6}$-hydrocarbyl group, or $R^1$ and $R^2$ together with the carbon atom to which they are attached, form a cyclohexane ring, and/or $R^3$ and $R^4$, together with the carbon atom to which they are attached, form a cyclohexane ring, and/or $R^5$ and $R^6$, together with the carbon atom to which they are attached, form a cyclohexane ring; or $R^1$ and R'together with the carbon atoms to which they are attached, form a benzene ring, or $R^3$ and $R^5$, together with the carbon atoms to which they are attached, form a benzene ring.

2. The composition of claim 1 wherein X is $-CH_2-$ or $-C(CH_3)_2-$.

3. The composition of claim 1 which contains a complex with zinc.

4. The composition of claim 1 which contains at least one compound or one complex which is
2-hydroxy-2,3-dihydro-1H-isoindol-1-thione/zinc 2:1 complex;
1-acetoxy-2-pyrrolidinthione;
a 1-hydroxy-2-pyrrolidinthione/zinc 2:1 complex;
1-acetoxy-5,5-dimethyl-2-pyrrolidinthione; or
a 5,5-dimethyl-1-hydroxy-2-pyrrolidinthione/zinc 2:1 complex.

5. The composition of claim 1 wherein the compound of formula I, or a salt or complex thereof, is in solution, suspension or emulsion in a liquid.

6. The composition of claim 1 wherein the carrier is a water soluble solid material.

7. The composition as claimed of claim 1 which contains from 0.0001% up to 50% by weight, of the composition, of the compound of formula I or a salt or complex thereof.

8. A method for inhibition of the growth of microorganisms on, or in, a medium which comprises treating the medium with a compound of the formula I:

or a salt or complex thereof, or with a biocide composition which contains a compound of the formula I or a salt or complex thereof with a metal of Group VIII, IB or IIB of the Periodic Table,
X is a group $-CR^1R^2-$ or a group $-CR^1=$;
Y is a group $-CR^3R^4-$ or a group $-CR^3=$;
Z is a group $-CR^5R^6-$ or a group $-CR^5=$;
R is a hydrogen or an acyl group; and
$R^1$ to $R^6$ are each, independently, a hydrogen atom or a $C_{1-6}$-hydrocarbyl group, or $R^1$ and $R^2$ together with the carbon atom to which they are attached, form a cyclohexane ring, and/or $R^3$ and $R^4$, together with the carbon atom to which they are attached, form a cyclohexane ring, and/or $R^5$ and $R^6$ together with the carbon atom to which they are attached, form a cyclohexane ring; or $R^1$ and $R^3$ together with the carbon atoms to which they are attached, form a benzene ring, or $R^3$ and $R^5$, together with the carbon atoms to which they are attached, form a benzene ring.

9. The method of claim 8 wherein the biocide composition or the compound, salt or complex:is incorporated or impregnated into the medium in an amount to provide from 0.001 up to 2% by weight of the compound, salt or complex relative to the weight of the medium.

10. The method of claim 8 wherein at least one further antimicrobial compound is used.

11. A biocide composition which contains an effective amount of at least one compound of the formula I which is a complex with a metal of group VIII, IB or IIB of the Periodic Table:

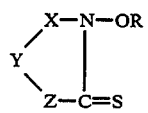

together with a carrier material, wherein
X is a group —$CR^1R^2$— or a group —$CR^1$=;
Y is a group —$CR^3R^4$— or a group —$CR^3$=;
Z is a group —$CR^5R^6$— or a group —$CR^5$=;
R is a hydrogen or an acyl group;
$R^1$ to $R^6$ are each, independently, a hydrogen atom or a $C_{1-6}$-hydrocarbyl group, or $R^1$ and $R^2$ together with the carbon atom to which they are attached, form a cyclohexane ring, and/or $R^3$ and $R^4$ together with the carbon atom to which they are attached, form a cyclohexane ring, and/or $R^5$ and $R^6$, together with the carbon atom to which they are attached, form a cyclohexane ring; or $R^1$ and $R^3$ together with the carbon atoms to which they are attached, form a benzene ring, or $R^3$ and $R^5$ together with the carbon atoms to which they are attached, form a benzene ring.

12. A method for inhibiting the growth of microorganisms on, or in, a medium which comprises treating the medium with a compound of the formula I:

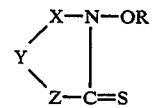 (I)

or complex thereof with a metal or group VIII, IB or IIB of the Periodic Table, or with a biocide composition which contains a compound of the formula I or complex thereof,
wherein
X is a group —$CR^1R^2$— or a group —$CR^1$=;
Y is a group —$CR^3R^4$— or a group —$CR^3$=;
Z is a group —$CR^5R^6$— or a group —$CR^5$=;
R is a hydrogen or an acyl group; and
$R^1$ to $R^6$ are each, independently, a hydrogen atom or a $C_{1-6}$-hydrocarbyl group or $R^1$ and $R^2$, together with the carbon atom to which they are attached, form a cyclohexane ring, and/or $R^3$ and $R^4$, together with the carbon atom to which they are attached, form a cyclohexane ring, and/or $R^5$ and $R^6$, together with the carbon atom to which they are attached, form a cyclohexane ring; or $R^1$ and $R^3$ together with the carbon atoms to which they are attached, form a benzene ring, or $R^3$ and $R^5$, together with the carbon atoms to which they are attached, form a benzene ring.

13. The composition of claim 1 wherein R is acetyl.

14. The composition of claim 1 wherein the compound is 5,5-dimethyl-1-hydroxy-2-pyrrolidinthione as a 2:1 zinc complex.

* * * * *